(12) United States Patent
Zellhuber et al.

(10) Patent No.: US 10,730,811 B2
(45) Date of Patent: Aug. 4, 2020

(54) PROCESS AND PLANT FOR PRODUCING OLEFINS

(71) Applicant: LINDE AKTIENGESELLSCHAFT, München (DE)

(72) Inventors: Mathieu Zellhuber, Martinsried (DE); Andreas Peschel, Wolfratshausen (DE); Helmut Fritz, München (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 16/472,625

(22) PCT Filed: Dec. 22, 2017

(86) PCT No.: PCT/EP2017/084333
§ 371 (c)(1),
(2) Date: Jun. 21, 2019

(87) PCT Pub. No.: WO2018/115414
PCT Pub. Date: Jun. 28, 2018

(65) Prior Publication Data
US 2019/0382324 A1    Dec. 19, 2019

(30) Foreign Application Priority Data

Dec. 22, 2016  (EP) .................................. 16206418

(51) Int. Cl.
*C07C 5/48* (2006.01)
*B01D 53/14* (2006.01)
*B01D 53/18* (2006.01)
*B01J 12/00* (2006.01)

(52) U.S. Cl.
CPC ............ *C07C 5/48* (2013.01); *B01D 53/1406* (2013.01); *B01D 53/1456* (2013.01); *B01D 53/1493* (2013.01); *B01D 53/18* (2013.01); *B01J 12/00* (2013.01); *B01D 2252/103* (2013.01)

(58) Field of Classification Search
CPC .. C07C 5/48; C07C 11/04; C07C 7/04; C07C 7/167; C07C 2523/22; C07C 2523/28; C07C 2523/648; C07C 2523/652; C07C 2523/656; C07C 2527/057; C07C 51/16; C07C 67/04; B01D 2252/103; B01D 53/1406; B01D 53/1456; B01D 53/1493; B01D 53/18
See application file for complete search history.

(56) References Cited

U.S. PATENT DOCUMENTS

2014/0249339 A1*  9/2014  Simanzhenkov .... B01J 19/0046
585/252

FOREIGN PATENT DOCUMENTS

| EP | 2716622 A1 | 4/2014 |
| EP | 3029402 A1 | 6/2016 |

OTHER PUBLICATIONS

PCT/EP2017/084333 International Search Report and Written Opinion dated Apr. 11, 2018, 8 pages.
PCT/EP2017/084333 International Preliminary Report on Patentability dated Jul. 4, 2019, 16 pages.

* cited by examiner

*Primary Examiner* — Sharon Pregler
(74) *Attorney, Agent, or Firm* — Lathrop GPM LLP

(57) ABSTRACT

A process for producing ethylene is proposed in which an ethane- and oxygen-containing reaction input is formed and a portion of the ethane and of the oxygen in the reaction input is converted into ethylene and into acetic acid by oxidative dehydrogenation to obtain a process gas, wherein the process gas contains the unconverted portion of the ethane and of the oxygen, the ethylene and the acetic acid and also water and wherein the process gas is subjected to a water quench. It is provided that the water quench comprises introducing the process gas into a scrubbing column (10, 20, 30, 40, 50) into which in at least two different column portions respective aqueous, liquid scrubbing medium streams are introduced and run in countercurrent to the process gas. A corresponding plant (100) likewise forms part of the subject matter of the invention.

20 Claims, 5 Drawing Sheets

PROCESS AND PLANT FOR PRODUCING OLEFINS

The invention relates to a process for producing olefins and a corresponding plant according to the preambles of the independent claims.

PRIOR ART

Oxidative dehydrogenation (ODH) of paraffins having two to four carbon atoms is known in principle. In ODH the recited paraffins are reacted with oxygen to afford inter alia olefins of identical carbon number and water.

ODH may be advantageous compared to established processes for producing olefins such as steamcracking or catalytic dehydrogenation. For instance, there is no thermodynamic equilibrium limitation on account of the exothermicity of the reactions involved. The formation energies $\Delta G$ for ethane, propane and n-butane are −102, −115 and −118 kJ/mol respectively. ODH may be performed at comparatively low reaction temperatures. Regeneration of the employed catalysts is in principle not necessary since the presence of oxygen allows an in situ regeneration. Finally, compared to steamcracking smaller amounts of worthless byproducts such as coke are formed.

For further details concerning ODH reference is made to the relevant technical literature, for example Ivars, F. and López Nieto, J. M., Light Alkanes Oxidation: Targets Reached and Current Challenges, in: Duprez, D. and Cavani, F. (ed.), Handbook of Advanced Methods and Processes in Oxidation Catalysis: From Laboratory to Industry, London 2014: Imperial College Press, pages 767-834, or Gärtner, C. A. et al., Oxidative Dehydrogenation of Ethane: Common Principles and Mechanistic Aspects, ChemCatChem, vol. 5, no. 11, 2013, pages 3196 to 3217 The invention is hereinbelow described in particular having regard to ODH of ethane (so-called ODH-E). However, the use of said invention is in principle possible and advantageous also for ODH of higher paraffins such as propane and butane. A reactor device and a process for oxidative dehydrogenation of alkanes is for example also known from EP 2 716 622 A1.

Particularly when using MoVNbTeOx catalysts under industrially relevant reaction conditions ODH forms significant amounts of the respective carboxylic acids of the employed paraffins as byproducts. For economic plant operation corresponding joint production of olefins and the respective carboxylic acids is generally necessary when using the described catalyst type. This applies in particular to ODH-E in which acetic acid is simultaneously formed. In addition ODH forms appreciable amounts of inter alia carbon monoxide and carbon dioxide as byproducts which together with water, carboxylic acids, residual oxygen and residual ethane are present in a gas mixture formed in ODH and must be removed from the respective primary products, i.e. the olefin(s) generated.

US 2014/0249339 A1 discloses subjecting such a gas mixture to a water quench to cool, and to scrub water-soluble components out of, said mixture. The present invention has for its object to improve such water quenches.

DISCLOSURE OF THE INVENTION

Against this background, the present invention proposes a process for producing olefins and a corresponding plant having the features of the independent claims. Embodiments are in each case subject matter of the dependent claims and of the description which follows.

Material streams, gas mixtures etc. may in the context of the present usage be rich or poor in one or more components, wherein the indication "rich" may represent a content of not less than 99%, 99.5%, 99.9% or 99.99% and the indication "poor" may represent a content of not more than 1%, 0.5%, 0.1% or 0.01% on a molar, weight or volume basis. If a plurality of components are reported the indication "rich" or "poor" relates to the sum of all components. If reference is made for example to "oxygen" or "ethane" a pure gas or else a mixture rich in the respective component may be concerned.

Material streams, gas mixtures etc. may in the context of the present usage also be "enriched" or "depleted" in one or more components, wherein these terms are based on a content in a starting mixture. They are "enriched" when they contain not less than 1.5 times, 2 times, 5 times, 10 times, 100 times or 1000 times the content, and "depleted" when they contain not more than 0.75 times, 0.5 times, 0.1 times, 0.01 times or 0.001 times the content, of one or more components based on the starting mixture.

The terms "pressure level" and "temperature level" are used hereinbelow to characterize pressures and temperatures, these being intended to express that pressures and temperatures need not be used in the form of exact pressure/temperature values. A pressure level or temperature level may for example be within ±1%, 5%, 10%, 20% or 50% of a mean value. A plurality of pressure and temperature levels may represent disjoint or overlapping ranges. The same pressure/temperature level may for example still be present even when pressures and temperatures have been reduced on account of transmission losses or cooling. Pressure levels reported here in bar are absolute pressures.

A "rectification column" is in the context of the present usage a separating unit adapted for at least partly fractionating a substance mixture injected in gaseous or liquid form or in the form of a biphasic mixture having liquid and gaseous proportions, optionally also in the supercritical state, by rectification, i.e. respectively generating from the substance mixture pure substances or at least substance mixtures having different compositions. Rectification columns are typically configured as cylindrical metal containers provided with internals, for example separating trays or ordered or unordered packings. A rectification column comprises a bottoms evaporator. This is a device having a heat exchanger which is heated and adapted for heating a liquid fraction accumulating in the bottom of the rectification column, also known as bottoms liquid. By means of a bottoms evaporator a portion of the bottoms product is continuously evaporated and recycled in gaseous form in the separating region.

The term "inert components" is to be understood here as meaning uncondensed gaseous proportions of a gas mixture which are unreactive in ODH, for example noble gases such as argon, but also compounds such as methane.

As mentioned at the outset, particularly when using MoVNbTeOx catalysts ODH can form significant amounts of the respective carboxylic acids of the employed paraffins as byproducts. Further byproducts are inter alia carbon monoxide and carbon dioxide. A gas mixture withdrawn from an ODH reactor typically further contains reaction and process water, residual oxygen and residual ethane. Such a gas mixture is referred to here as "process gas" of ODH. As mentioned the process gas contains one or more olefins as primary product(s) and also byproducts and unconverted reactants.

Advantages of the Invention

As mentioned at the outset water quenches are known for treatment of process gases from ODH. However, particularly when such gas mixtures contain appreciable amounts of one or more carboxylic acids such as acetic acid such known processes prove unsatisfactory because the carboxylic acid(s) is/are scrubbed out only inadequately. This can have negative effects particularly on downstream process steps. These are described below with reference to acetic acid and thus the example of ODH-E. However, corresponding elucidations also apply (with limitations) for higher carboxylic acids.

Acetic acid and water have very similar boiling points and are accordingly difficult to separate from one another by distillation. The result of this is that in the case of insufficient removal even during further processing of the process gas a condensation of water and acetic acid may occur, which takes place largely simultaneously. An aqueous condensate therefore always has an appreciable acid proportion which will be close to the acetic acid/water ratio in the process gas directly downstream of the reactor(s) used.

In other words in the case of insufficient removal of the acetic acid, acid-containing condensates can appear in large parts of the separation and in devices used therein. Upon application of a separating concept typical for olefin plants this would mean that in the entire quenching and compressor section high acetic acid concentrations may partly occur. This entails additional cost and complexity in terms of material choice and/or may markedly reduce the longevity of such plants.

In addition to this, process units for carbon dioxide removal which may be provided, for example an amine scrub and/or a lye scrub, are negatively affected in their mode of operation by appreciable amounts of acetic acid in the product gas.

It is an achievement of the process provided according to the invention that the acetic acid formed during ODH may be largely removed already in the first step or in an early step of a corresponding separation. The process according to the invention further ensures good heat integration and a low pressure drop in the system.

To achieve these advantages the present invention proceeds from a process for producing ethylene known in principle in which an ethane- and oxygen-containing reaction input is formed and a portion of the ethane and of the oxygen in the reaction input is converted into the ethylene and into acetic acid by oxidative dehydrogenation to obtain a process gas, wherein the process gas contains the unconverted portion of the ethane and of the oxygen, the ethylene and the acetic acid and also water and wherein the process gas is subjected to a water quench. Details have already been elucidated.

According to the invention it is now provided that the water quench comprises introducing the process gas into a scrubbing column into which in at least two different column portions respective aqueous, liquid scrubbing medium streams are introduced and run in countercurrent to the process gas. In this way improved heat integration can be achieved by undertaking selective temperature control of the different scrubbing medium streams and the content of acetic acid can be reduced to values acceptable for downstream units particularly also in the embodiments elucidated hereinbelow. In each case a process gas that is in particular cooled and at least largely purified of acetic acid is withdrawn from the top of the scrubbing column.

According to a preferred embodiment of the process according to the invention a scrubbing column having a first column portion and a second column portion is used, wherein the second column portion is arranged above the first column portion, the process gas is introduced into a lower region of the first column portion and partly or completely allowed to ascend through the first column portion, from the first column portion into the second column portion and through the second column portion and in an upper region of the first column portion a first liquid scrubbing medium stream, and in an upper region of the second column portion a second liquid scrubbing medium stream, is introduced.

The term "different column portions" is to be understood as meaning in the parlance used here regions of a scrubbing column which exhibit no spatial overlap with one another. In particular different column portions are regions arranged at different heights. The different column portions have (identical or different) exchange structures which are in particular adapted for increasing the size of a surface area of the scrubbing medium trickling down in the respective column portions and thus ensuring an improved exchange with the process gas. In particular to this end the column portions may comprise the previously described internals, for example separating trays or ordered or unordered packings.

A "lower" region of a column portion is here to be understood as meaning a region which ends at less than 50%, in particular less than 40%, 30%, 20% or 10%, of the height of the respective column portion. Accordingly, an "upper" region of a column portion is here to be understood as meaning a region which starts at more than 50%, 60%, 70%, 80% or 90% of the height of the column portion.

It is advantageous when the first scrubbing medium stream is introduced at a first temperature level into the first column portion and the second scrubbing medium stream is introduced at a second temperature level into the second column portion. In particular the first temperature level may be at 50° C. to 90° C. and/or the second temperature level at 20° C. to 50° C. At such temperatures an advantageous heat integration may be effected whereby to provide the first temperature level for example a material stream flowing in a corresponding plant, and to provide the second temperature level cooling water, are at least partly used. In principle in the context of the present invention heat-integrated heat exchangers, i.e. heat exchangers operated with material streams flowing in a corresponding plant such as input or product streams, and so-called "utility" heat exchangers, i.e. heat exchangers operated with a separate medium, may in each case be employed alone or in any desired combination with one another.

In the context of the present invention it may be provided that the process gas is brought into contact in the first (lower) column portion with the entire (combined) liquid of both scrubbing medium streams and in the second (upper) column portion only with the liquid of the second scrubbing medium stream. However, alternatively to this first variant it is also possible according to a second variant to bring the process gas into contact in the first column portion only with the liquid of the first scrubbing medium stream and in the second column portion only with the liquid of the second scrubbing medium stream. In the second variant it is possible for the first and the second scrubbing medium stream to have different contents of in particular acetic acid. In particular the second scrubbing medium stream may have a lower content of acetic acid than the first so that an improved scrubout may be undertaken.

The just now elucidated first variant comprises in particular that liquid is withdrawn from a lower region of the first column portion and partly or completely used for forming the first and the second scrubbing medium stream. In other words such liquid can thus be divided and partly employed in the form of or as part of the first scrubbing medium stream and partly employed in the form of or as part of the second scrubbing medium stream. Due to this formation of the first and of the second scrubbing medium stream, said streams in particular have the same contents of acetic acid and of other compounds. This variant is illustrated in particular with reference to the accompanying FIG. 3A.

The just now elucidated second variant is in particular realized when the first column portion is separated from the second column portion by a liquid barrier tray and in particular liquid is withdrawn from a lower region of the first column portion and partly or completely used in the formation of the first scrubbing medium stream and liquid is withdrawn from a lower region of the second column portion.

The liquid withdrawn from the lower region of the second column portion may in the second variant be partly or completely used in the formation of the second scrubbing medium stream. If the liquid withdrawn from the lower region of the second column portion is in the second variant not or not completely used in the formation of the second scrubbing medium stream the liquid withdrawn from the lower region of the second column portion or a remaining proportion may also be discharged or used in the formation of the first scrubbing medium stream. The second scrubbing medium stream may in the second variant in particular also be formed such that it comprises no liquid withdrawn from the lower region of the second column portion. In this way a single pass of the second scrubbing medium stream may be achieved.

In all elucidated cases the second scrubbing medium stream may comprise fresh water, i.e. for example demineralized water, and/or purified water from a further process unit, in particular an acetic acid recovery unit. If the second scrubbing medium stream as elucidated is formed such that it comprises no liquid withdrawn from the lower region of the second column portion the second scrubbing medium stream may also consist completely of such fresh/demineralized water and/or purified water. Admixing of further liquids to the second scrubbing medium stream is also possible. Purified water from an acetic acid recovery unit contains for example about 0 to 5000 ppmw of acetic acid.

The use of the liquid barrier tray through which gas may ascend but no liquid can flow away downward prevents in the second variant liquid of the first and of the second scrubbing medium stream undergoing appreciable and uncontrolled mixing in the column. This variant is illustrated in particular with reference to the accompanying FIG. 3B.

The two scrubbing medium streams can in this second variant therefore have the previously elucidated different contents. In this way in ascending direction an increasingly pure scrubbing medium may be employed. In other words the first and the second scrubbing medium stream may contain predominantly water and the first scrubbing medium stream may have a higher acetic acid content than the second scrubbing medium stream.

An expansion of the elucidated first or the elucidated second variant, described here as the third variant, comprises using a scrubbing column having a third column portion above the second column portion, wherein the process gas is partly or completely allowed to ascend from the second column portion into the third column portion and through the third column portion, a third liquid scrubbing medium stream is introduced in an upper region of the third column portion and in particular liquid is withdrawn from a lower region of the third column portion. In this third variant an even purer tops product of the scrubbing column can be obtained. A liquid barrier tray or a further liquid barrier tray is in particular arranged between the second and the third column portion here.

In the third variant a first embodiment is possible in which a single pass of the third scrubbing medium stream is undertaken, i.e. at the top of the scrubbing column the third scrubbing medium stream is introduced and from a lower region of the third column portion, above the liquid barrier tray, liquid is withdrawn but no longer recirculated, i.e. used in the formation of the third scrubbing medium stream. The liquid may for example be used in the formation of the second scrubbing medium stream and/or discharged. In this way in particular a high-purity third scrubbing medium stream can always be provided. This is illustrated in particular with reference to FIG. 4B. By contrast a second embodiment of the third variant provides a corresponding circuit as is also shown in particular in FIG. 4A.

In the first embodiment of the third variant the liquid withdrawn from the lower region of the third column portion is thus in particular partly or completely used in the formation of the second scrubbing medium stream or discharged. By contrast in the second embodiment of the third variant the liquid withdrawn from the lower region of the third column portion is partly or completely used in the formation of the third scrubbing medium stream. In each case the third scrubbing medium stream contains predominantly water and advantageously not more than 5000 ppmw of acetic acid.

In the first embodiment of the third variant the third scrubbing medium stream may be formed from fresh water, i.e. for example demineralized water, or else also for example from the mentioned purified water from a further process unit, in particular an acetic acid recovery unit, or the third scrubbing medium stream may at least comprise such water. For details reference is made to the corresponding remarks concerning the second variant. But also in the second embodiment of the third variant the third liquid scrubbing medium stream may comprise such water in addition to the liquid withdrawn from the lower region of the third column portion.

In the third variant, in particular in the first embodiment, a chemical scrub using lye for example may also be performed in the third column portion. An aqueous lye or waste lye stream, i.e. an alkaline solution comprising one or more suitable organic or inorganic components, may thus be used as the third scrubbing medium stream or as a portion of the third scrubbing medium stream. Here, either fresh lye, for example aqueous sodium hydroxide solution, or waste lye from a downstream lye scrub for treatment of the process gas and/or a mixture of the recited liquids may be used. In this way, in particular a further utilization of such waste lye from a lye scrub may be undertaken before said lye is supplied to a waste lye unit. This improves the exploitation of the lye.

An expansion of the elucidated third variant, described here as the fourth variant, provides that a scrubbing column having a fourth column portion above the third column portion is used, wherein the process gas is partly or completely allowed to ascend from the third column portion into the fourth column portion and through the fourth column portion, a fourth liquid scrubbing medium stream is introduced in an upper region of the fourth column portion and liquid is withdrawn from a lower region of the fourth column portion. In this embodiment in the uppermost (fourth) column portion in particular the chemical scrub using lye, as already elucidated with reference to the second variant, may be performed. Thus here too in particular an aqueous lye or waste lye stream, i.e. an alkaline solution of one or more suitable organic or inorganic components, is used as the fourth scrubbing medium stream or as a portion thereof. Here too, either fresh lye, for example aqueous sodium hydroxide solution, or waste lye from a downstream lye scrub for treatment of the process gas and/or a mixture of the recited lyes may be used. Thus in this case too in particular a further utilization of such waste lye may be undertaken before said lye is supplied to a waste lye unit. As mentioned, this improves the exploitation of the lye. This variant is shown in FIG. 5 in particular.

However, it is also possible in principle that the fourth scrubbing medium stream is formed from fresh water, i.e. for example demineralized water, or else also for example from the purified water from a further process unit, in particular an acetic acid recovery unit, as already elucidated above in connection with the second and third variant or at least comprises such water. However, it is also possible to form the fourth scrubbing medium stream using liquid withdrawn from a lower region of the fourth column portion. All alternatives may also be employed in combination.

Likewise forming part of the subject matter of the present invention is a plant for producing ethylene adapted for forming an ethane- and oxygen-containing reaction input and for converting a portion of the ethane and of the oxygen in the reaction input into the ethylene and into acetic acid by oxidative dehydrogenation to obtain a process gas, wherein the process gas contains the unconverted portion of the ethane and of the oxygen, the ethylene and the acetic acid and also water and wherein means adapted for subjecting the process gas to a water quench are provided.

According to the invention it is provided that in such a plant for water quenching a scrubbing column having at least two different column portions is provided, means adapted for introducing the process gas into the scrubbing column are provided and means adapted for introducing respective aqueous, liquid scrubbing medium streams into the at least two different column portions and running them in countercurrent to the process gas are provided.

For features and advantages of a corresponding plant reference is made to the above elucidations concerning the features and advantages of the process. In particular such a plant is adapted for performing a process according to the specific embodiments elucidated above and comprises means suitable therefor. In this regard too reference is made to the above intimations.

The invention is more particularly elucidated below with reference to the appended drawings which illustrate inter alia preferred embodiments of the present invention.

DETAILED DESCRIPTION OF THE DRAWINGS

Figure 1:
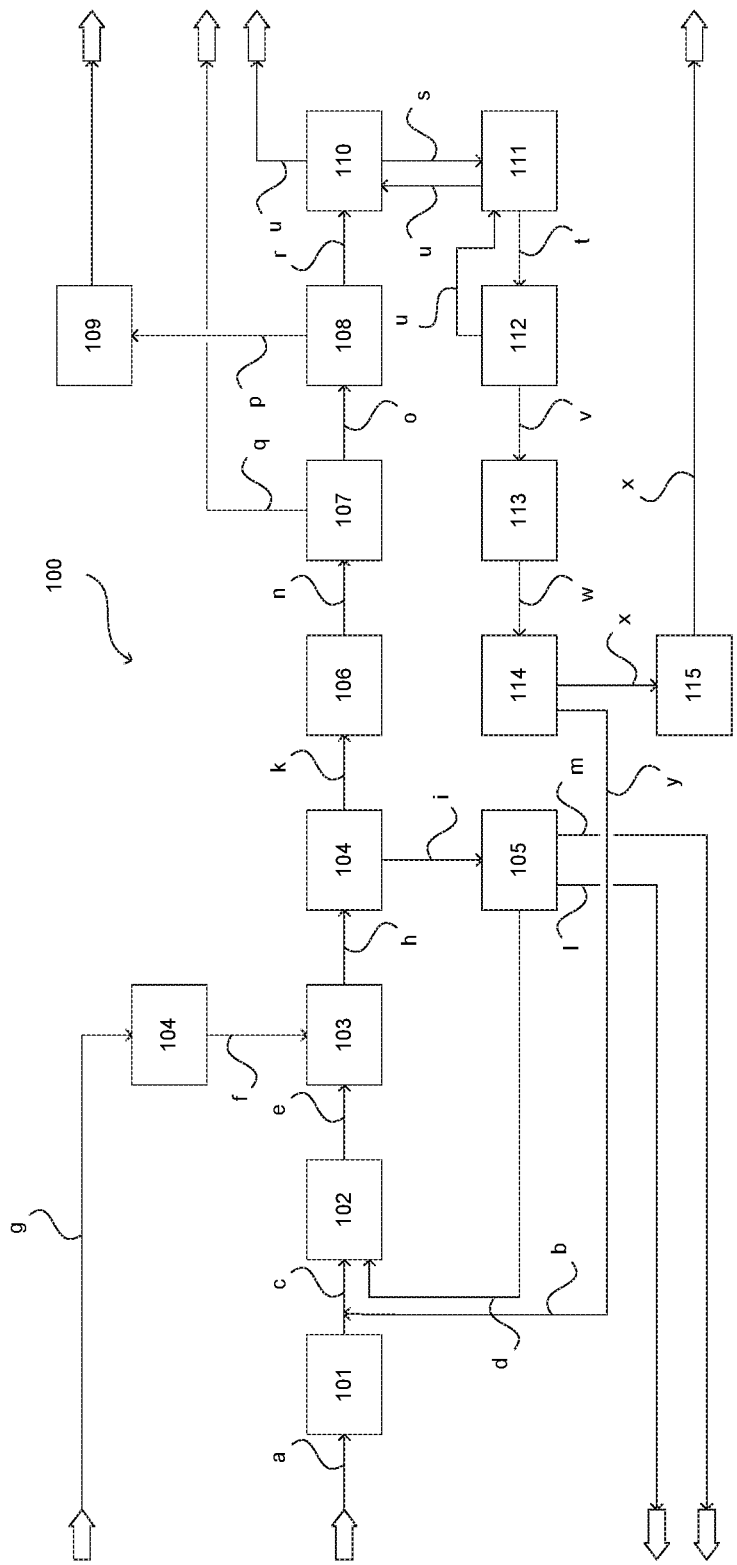
FIG. 1 shows a plant for producing olefins according to one embodiment of the invention.

In the figures that follow functionally or structurally equivalent elements are indicated with identical reference numerals and for the sake of simplicity are not repeatedly elucidated. When plant parts are described hereinbelow the elucidations concerning these also apply correspondingly to the process steps implemented by means of these plant parts and vice versa.

In FIG. 1 a plant for producing olefins according to one embodiment of the invention in the form of a greatly simplified plant diagram is illustrated and collectively referred to as 100. Notwithstanding that a plant 100 for ODH of ethane (ODH-E) is described below, the present invention is also suitable, as mentioned, for use in ODH of higher hydrocarbons. In this case the elucidations which follow apply correspondingly.

In the plant 100 a separation input in the form of a material stream a is supplied to a rectification unit 101 having for example one or more rectification columns and subjected to a rectification. In the depicted example the separation input contains at least ethane and higher hydrocarbons, in particular corresponding higher paraffins. The rectification unit 101 may also be supplied with one or more further separation inputs.

In the rectification unit 101 the separation input is subjected to a rectification alone or together with the further separation input(s) to obtain a separation product which contains ethane but is poor in higher hydrocarbons. The separation product is withdrawn in the form of a material stream c and supplied to a preheating unit 102. In the preheating unit 102 the separation product is preheated, wherein in the depicted example the preheating unit 102 is also supplied with a water or steam stream d. Further material streams may also be supplied. A further material stream b elucidated below may be added to the material stream c.

A material stream e outflowing from the preheating unit 102 is supplied to a reaction unit 103 to form a reaction input. On account of its formation using the separation product from the rectification unit 101 the reaction input contains ethane but is poor in higher hydrocarbons. The reaction input may further contain one or more diluents such as water or inert gases and further components. These may also be supplied to the reaction unit 103 in the form of further material streams (not shown).

In the depicted example the reaction unit 103 is supplied with an oxygen-containing material stream f. This may be provided using an air separation plant 104. To this end the air separation plant 104 is supplied with an airstream g. The oxygen-containing material stream f may be substantially pure oxygen but fractions of nitrogen and of noble gases may also be present depending on the operation of the air separation plant 104. In this way it is likewise possible to supply diluent.

Outflowing from the reaction unit 103 is a process gas in the form of a process gas stream h which contains ethylene formed in the reaction unit 103 by ODH of a portion of the ethane in the reaction input. The product mixture further contains acetic acid likewise formed from ethane during ODH in the reaction unit 103, water, carbon monoxide, carbon dioxide, unconverted oxygen and the diluent(s) and further compounds if added or previously formed in the reaction unit 103.

It will be appreciated that reaction unit 103 may comprise a or else a plurality of reactors which are for example operated in parallel. In the latter case these reactors are each supplied with corresponding reaction inputs, which may have identical or different compositions, and corresponding oxygen-containing material streams f and in each case corresponding process gas streams h are formed. The latter may for example be combined and supplied together as process gas to the units elucidated below.

The process gas is transferred into a quench unit 104 in which, for example in a scrubbing column, it may be contacted with quench water or a suitable aqueous solution. In the quench unit 104 the process gas is in particular cooled and the acetic acid formed in the reaction unit 103 is scrubbed out of the process gas. Acetic acid-laden process water outflows from the quench unit 104 in the form of a material stream i, the process gas at least largely freed of acetic acid outflows from the quench unit 104 in the form of a material stream k.

In an optional acetic acid recovery unit 105 acetic acid is separated off from the acetic acid-laden process water as glacial acetic acid which is discharged from the plant 100 as material stream I. Pure process water likewise recovered in the acetic acid recovery unit 105 may be supplied to the preheating unit 102 in the form of the previously elucidated material stream d. The process water supplied to the reactor may also be partly or completely provided in the form of externally supplied freshwater. Water that is no longer usable or required may be discharged from the plant 100 and supplied to a wastewater treatment in the form of a wastewater stream m.

The process gas present in the form of material stream k and at least largely freed of acetic acid is compressed to a suitable pressure level, for example 15 to 25 bar, in a compressing unit 106 and in the form of a compressed material stream n supplied to an amine scrub unit 107. Scrubbed out therein are in particular portions of the carbon dioxide present in the process gas. After regeneration of the amine the scrubbed-out carbon dioxide may be discharged from the plant in the form of a material stream q.

The process gas thus partly freed of carbon dioxide is transferred in the form of a material stream o into a lye scrub unit 108 and further purified of carbon dioxide therein. Generated in the lye scrub unit 108 is waste lye which in the form of a material stream p is transferred into a waste lye treatment unit 109 and finally discharged from the plant.

The process gas further purified in the lye scrub unit 108 is transferred in the form of a material stream r into a precooling and drying unit 110 where it may be freed from residual water in particular. The dried process gas is transferred in the form of a material stream s into a low temperature unit 111 and subsequently in further-cooled form in the form of one or more material streams t into a demethanization unit 112. In the low temperature unit 111 and the demethanization unit 112 components lower boiling than ethylene, among them in particular carbon monoxide and oxygen, are separated off from the process gas, wherein the remainder stays in condensed form. If the process gas contains higher hydrocarbons formed as a byproduct during ODH in the reaction unit 103 these are likewise converted into condensate.

The separated-off components lower boiling than ethylene are recycled in the form of one or more material streams u through the low temperature unit 111 and the precooling and drying unit 110, therein optionally combined with further corresponding material streams, used for cooling purposes and discharged from the plant 100. If required the hydrocarbons having two and optionally more carbon atoms are supplied in the form of a material stream v to a hydrogenation unit 113 in which in particular acetylene likewise formed as byproduct during ODH in the reaction unit 103 may be hydrogenated. After the hydrogenation the material stream now referred to as w is transferred into an ethylene removal unit 114.

In the ethylene removal unit 114 ethylene is at least largely separated off from other components and in the form of a material stream x after utilization in an ethylene cooling unit 115 may be discharged from the plant 100 in gaseous form. The remaining components, predominantly ethane and possibly higher hydrocarbons, are withdrawn in the form of a material stream y and in the form of the material stream b recycled into the pre-heating unit 101.

Figure 2:
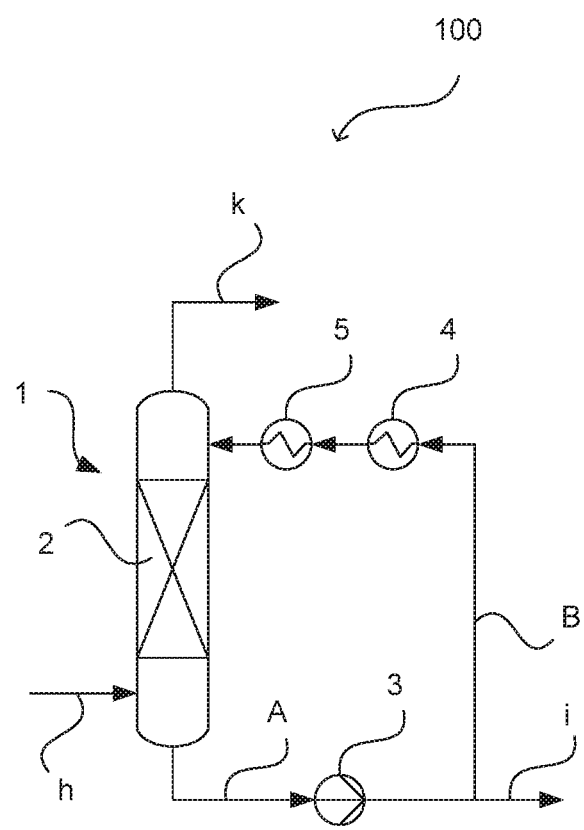
FIG. 2 shows a water quench according to a noninventive embodiment in schematic form.

FIG. 2 shows a water quench according to a noninventive embodiment and FIGS. 3A and 3B, 4A and 4B and 5 which follow each show water quenches according to embodiments of the present invention in schematic form. Elements 1 to 9 shown in the recited figures each fulfil identical or comparable functions and are therefore in principle of comparable construction. However, they may each be provided in different embodiments, for example in different sizes and in different quantities.

The material streams labelled with the same capital letters are likewise comparable in principle. The water quenches shown in the recited figures may be used as the quench unit 104 according to FIG. 1 or as a portion of such a quench unit, the integration thereof is achieved via the material streams labelled, here as there, h, i and k.

As repeatedly mentioned the present invention relates to a process for producing ethylene in which an ethane- and oxygen-containing reaction input is formed and a portion of the ethane and of the oxygen in the reaction input is converted into the ethylene and into acetic acid by oxidative dehydrogenation to obtain a process gas, wherein the process gas contains the unconverted portion of the ethane and of the oxygen, the ethylene and the acetic acid and also water.

This process gas which in particular also contains further components, for example carbon monoxide and carbon dioxide, is in the noninventive variant shown in FIG. 2 at a temperature level of for example about 140° C. in the form of the material stream labelled h as in FIG. 1 supplied to a scrubbing column 1.

The scrubbing column 1 comprises an exchange region 2 which may comprise suitable trays and/or dumped beds. From the bottoms region of the scrubbing column 1 a liquid fraction at a temperature level of for example about 80° C. to 100° C. in the form of a material stream A is withdrawn and partly by means of a pump 3 in the form of a material stream B passed through a heat exchanger 4 and a heat exchanger 5 and back into a top region of the scrubbing column 1.

In this way an aqueous, liquid scrubbing medium stream is formed and runs in countercurrent to the process gas. The liquid fraction accumulating in the bottom of the scrubbing column 1 is essentially a water-acetic acid mixture. Excess water-acetic acid mixture may be discharged in the form of the material stream labelled i as in FIG. 1. A cooled process gas may be withdrawn in the form of the material stream labelled k as in FIG. 1.

Via the heat exchanger 4 a heat integration is undertaken and the liquid fraction cooled to a temperature level of for example 50° C. to 90° C. In the heat exchanger 5 the liquid fraction is cooled to a temperature level of for example 20° C. to 50° C. by means of cooling water.

According to the variant shown in FIG. 2 a quench, i.e. a rapid cooling, having the aims of heat integration and greatest possible cooling coupled with a low pressure drop is undertaken. However, typically a comparatively low depletion of acetic acid is achieved.

However, this is achieved in the embodiments of the invention shown in FIGS. 3A and 3B, 4A and 4B and also 5 that follow in which the water quench comprises introducing the process gas into a respective scrubbing column into which in at least two different column portions respective aqueous, liquid scrubbing medium streams are introduced and run in countercurrent to the process gas.

Figure 3B:
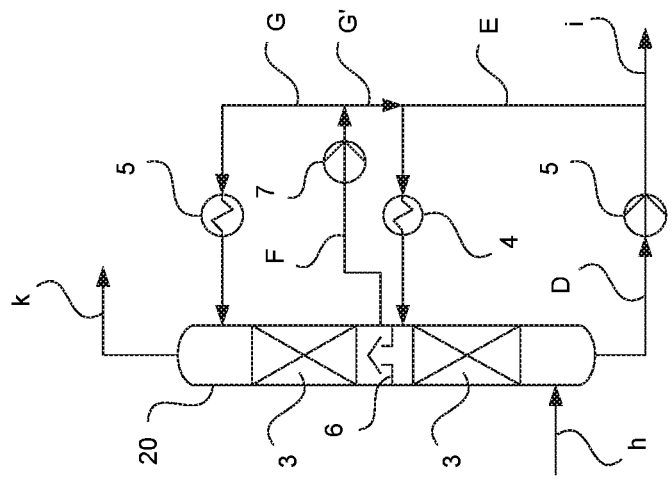
FIGS. 3A and 3B show water quenches according to embodiments of the present invention in schematic form.
Figure 3A:
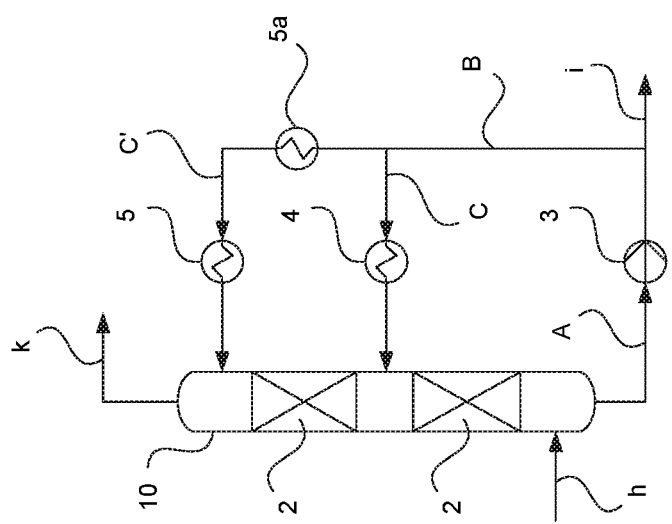

In the embodiment shown in FIG. 3A the scrubbing column is labelled 10. Said column comprises two exchange regions 2 which can each comprise suitable trays and/or dumped beds. In this way the scrubbing column 10 is divided. A substream C of the total circulating amount of the material stream B conveyed by means of the pump 3 is introduced via the heat exchanger 4 between the two exchange regions 2 into the scrubbing column 10. A further substream C' of the total circulating amount conveyed by means of the pump 3 is introduced via the heat exchanger 5 and a further, in particular heat-integrated, heat exchanger 5a into the top region of the scrubbing column 10.

The temperature levels are essentially the same as those elucidated previously in relation to the two scrubbing medium streams. According to the embodiment shown in FIG. 3A an air cooling may also be undertaken in the heat exchanger 5.

Compared to the embodiment shown in FIG. 2 the embodiment shown in FIG. 3A allows the temperature profile of the column to be better adjusted and accordingly also allows a higher degree of heat integration to be achieved since more energy may be removed at a higher temperature level.

In the embodiment shown in FIG. 3B two circuits completely separate from one another are provided which make it possible in particular to achieve a gradient in the acetic acid concentration from bottom to top and thus to reduce acetic acid introduction into a subsequent compression unit such as the compression unit 106 according to FIG. 1. In addition this measure yet further enhances the potential for heat integration.

To this end the scrubbing column labelled 20 here is divided by means of a liquid barrier tray 6, in particular by means of a chimney neck tray. The liquid withdrawn from the bottom of the scrubbing column 20 in the form of a material stream D is partly introduced via the heat exchanger 4 in the form of a material stream E below the liquid barrier tray 21 into a lower column portion of the scrubbing column 20.

A liquid collecting on the liquid barrier tray 6 is withdrawn at a temperature level of for example 40° C. to 70° C. in the form of a material stream F and in the form of a material stream G by means of a pump partly passed through the heat exchanger 7 and introduced at the top of the scrubbing column 20. A further proportion of the material stream F is in the form of a material stream G' passed into the lower scrubbing medium circuit and/or discharged. The discharging may, as not specially shown, be effected separately to that of the lower circuit where a proportion of the material stream D is discharged as material stream i or both discharge streams are passed out of the plant mixed together as material stream i.

Figures 4A, 4B:
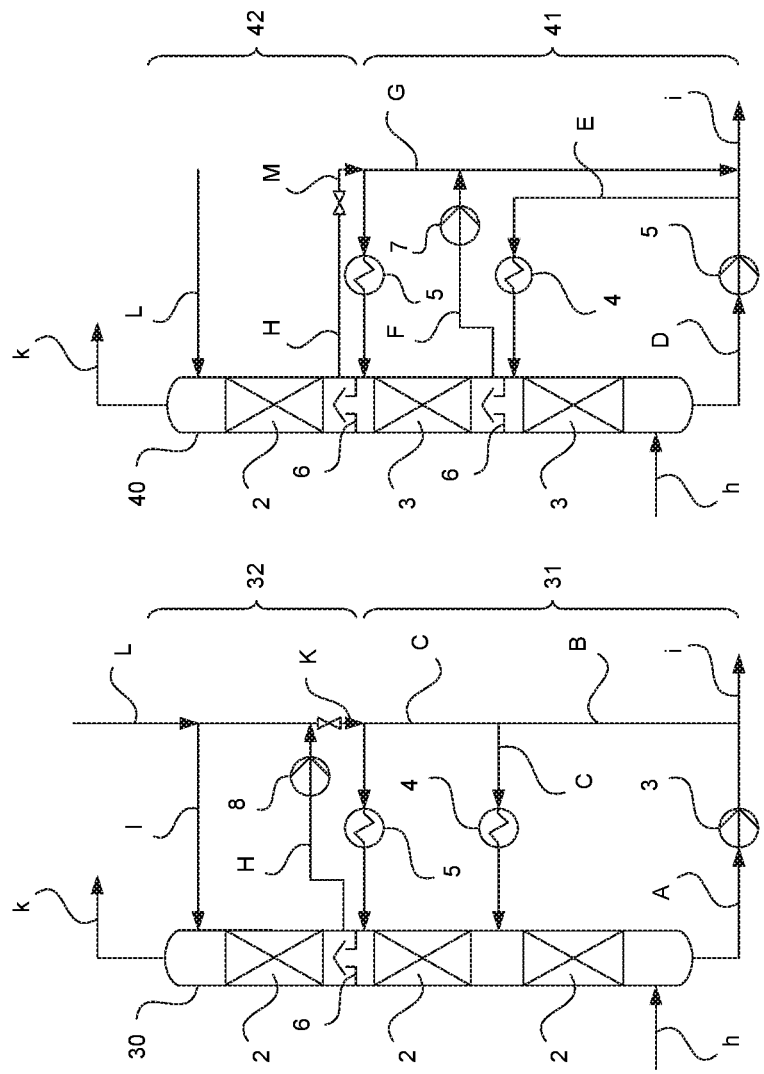
FIGS. 4A and 4B show water quenches according to embodiments of the present invention in schematic form.

Compared to the embodiments shown in FIGS. 2, 3A and 3B in the embodiments shown in FIGS. 4A and 4B an additional column portion is added, i.e. the scrubbing columns labelled 30 and 40 respectively are in their lower portion labelled 31 and 42 respectively configured similarly to the scrubbing columns depicted in FIGS. 2, 3A and 3B and comprise corresponding scrubbing medium circuits, internals etc.

This is not shown in all combinations merely for reasons of clarity. Thus in the depicted example the embodiment shown in FIG. 4A comprises the lower portion 31 according to the embodiment shown in FIG. 3A; however, the lower portion 31 may also be configured according to the embodiment shown in FIG. 3B. Correspondingly, in the depicted example the embodiment shown in FIG. 4B comprises the lower portion 41 according to the embodiment shown in FIG. 3B; however, the lower portion 41 may also be configured according to the embodiment shown in FIG. 3A.

The respective added column portions are labelled 32 and 42 respectively. Said portions are delimited from the lower portions 31 and 41 by means of a further liquid barrier tray. Above this liquid barrier tray 6 liquid is in each case withdrawn in the form of a material stream H.

According to the embodiment shown in FIG. 4A a pumped circuit comprising a pump 8 is provided by means of which at least a portion of the material stream H in the form of a material stream I at a temperature level of for example 20° C. to 50° C. may for example be recycled onto the top region of the column portion 32, mixed with a material stream L of fresh, demineralized water or else also for example purified water from an acetic acid recovery unit, for example acetic acid recovery unit 105 according to FIG. 1, comprising for example about 0 to 5000 ppmw of acetic acid. Excess liquid is, under fill-level control for example, supplied in the form of a material stream K to the material stream C or otherwise discharged.

According to the embodiment shown in FIG. 4B exclusively fresh, demineralized water or else also for example purified water from an acetic acid recovery unit, for example the acetic acid recovery unit 105 according to FIG. 1, comprising for example about 0 to 5000 ppmw of acetic acid and at a temperature level of for example 20° C. to 50° C. is applied to the top of the column portion 42 in the form of a material stream L. Excess liquid is, under fill-level control for example, supplied in the form of a material stream K to the material stream C or otherwise discharged. The material stream H is, under fill-level control for example, at least partly supplied in the form of a material stream M to the material stream G or otherwise discharged.

Figure 5:
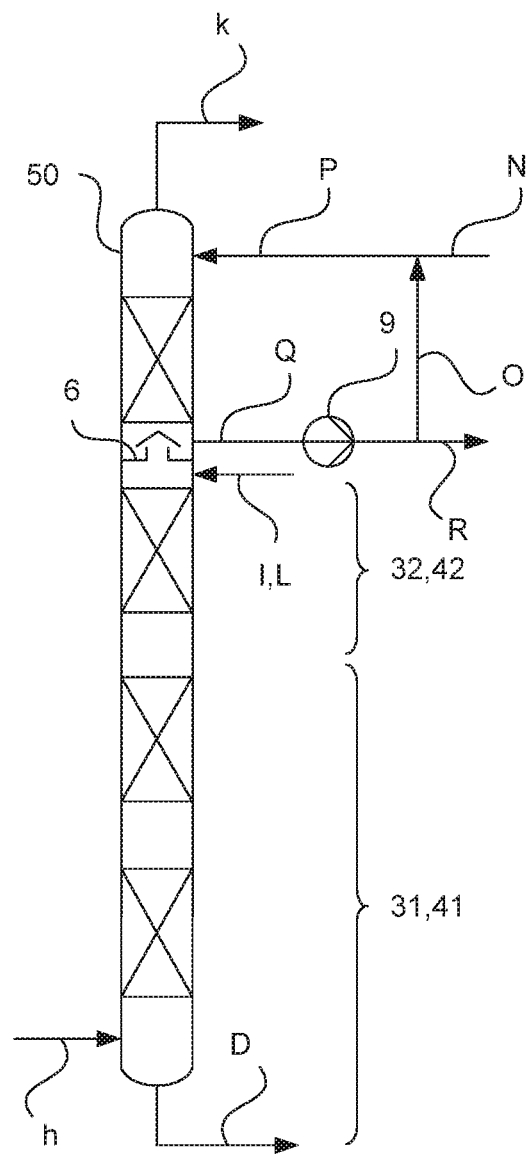
FIG. 5 shows a water quench according to an embodiment of the present invention in schematic form.

FIG. 5 shows an embodiment in which the embodiments shown in FIGS. 4A and 4B are expanded again. The portions 31 and sections 41 and 32 and 42 shown in FIGS. 4A and 4B may be provided here in any desired combination and are not shown in detail in FIG. 5 for reasons of generality.

In turn the uppermost column portion of the scrubbing column labelled 50 here is separated by a liquid barrier tray 6 from the column portions 31, 32, 41 and 42 below. This adds a further column portion which is integrated into a circuit pumped via a pump 9 into which either a waste lye stream from a downstream process unit such as for example the lye stream p from the lye scrubbing unit 108 according to FIG. 1, a fresh lye solution or a combination of both is introduced. A corresponding material stream is labelled N in FIG. 5.

Together with a circuit stream O the material stream M is applied to the top of the scrubbing column 50 as material stream P. Above the liquid barrier tray 6 laden lye Q is withdrawn. This may be partly used in the form of the circuit stream O and partly discharged as material stream R into a waste lye treatment unit such as the waste lye treatment unit 109 according to FIG. 1.

In this way in addition to backscrubbing with water a chemically based scrub is provided which further reduces the quantity of acetic acid passing overhead and thus protects downstream units.

The advantages achievable through the use of the embodiments of the present invention elucidated hereinabove are in summary once again elucidated with reference to corresponding simulation data hereinbelow.

In all cases it was assumed that the process gas introduced into the scrubbing column in each case is employed at a temperature of 140° C., a pressure of 2.1 bar (abs.) and in a mass flow of 110 t/h, wherein the content of acetic acid is 11.1 wt %, the content of water is 29 wt % and the content of hydrocarbons having two carbon atoms is 56.5 wt %.

In the noninventive embodiment according to FIG. 2, i.e. comprising one circuit and one recycle stream, the acetic acid can be separated from the process gas in a proportion of 99.4% and the acetic acid content in the tops stream of the scrubbing column (material stream k) is 5814.0 ppmw. The usable heat output at a temperature above 85° C. is 4428 kW, the circuit mass flow of the circulated scrubbing medium is 430 t/h and the fresh water consumption is 0 t/h.

In contrast thereto, while in the embodiment of the present invention shown in FIG. 3A comprising one circuit and two recycle streams acetic acid can be separated to the same extent of 99.4% and the acetic acid content in the tops stream also has a comparable value of 5890.0 ppmw, the usable heat output above 85° C. increases to a value of 4609 kW. As previously mentioned, compared to the noninventive embodiment shown in FIG. 2 the embodiment shown in FIG. 3A thus allows the temperature profile of the column to be better adjusted and accordingly also allows a higher degree of heat integration to be achieved since more energy may be removed at a higher temperature level. In this case the circuit mass flow is 730 t/h, the fresh water consumption is 0 t/h.

In the embodiment of the present invention shown in FIG. 3B comprising two circuits and two recycle streams a higher proportion of acetic acid of 99.6% may be separated. The acetic acid content in the tops stream is markedly reduced to a value of 3906.0 ppmw. In this way acetic acid introduction into subsequent units such as a compression unit can be markedly reduced. As likewise mentioned the heat integration may be yet further enhanced here. The usable heat output at a temperature of 85° C. is markedly increased here, namely to a value of 5833 kW. The circuit mass flow is 1140 t/h, the fresh water consumption is 0 t/h.

A further marked improvement in acetic acid removal is possible in the embodiment of the invention shown in FIG. 4A comprising one circuit, two recycle streams and fresh water purging. Altogether 99.98% by proportion of acetic acid can be separated here, leaving an acetic acid content in the tops stream of 177.0 ppmw. The usable heat output above 85° C. is 3828 kW, the circuit mass flow is 730 t/h and the fresh water consumption is 8 t/h.

The acetic acid removal in the embodiment of the invention shown in FIG. 4B comprising two circuits, two recycle streams and a fresh water purge results in a yet further improved acetic acid separation of 99.99% by proportion, leaving 90.0 ppmw of acetic acid in the tops stream. The usable heat output above 85° C. is 5116 kW, the circuit mass flow is 1140 t/h and the fresh water consumption is 8 t/h.

A downstream lye scrub, as provided in the embodiment shown in FIG. 5 downstream in an additional column portion, can afford a further marked reduction in the acetic acid content in the tops stream to a value typical for chemical scrubs, i.e. to a value of less than 1 ppmw.

The invention claimed is:

1. Process for producing ethylene in which an ethane- and oxygen-containing reaction input is formed and a portion of the ethane and of the oxygen in the reaction input is converted into ethylene and into acetic acid by oxidative dehydrogenation to obtain a process gas, wherein the process gas contains the unconverted portion of the ethane and of the oxygen, the ethylene and the acetic acid and also water and wherein the process gas is subjected to a water quench, characterized in that the water quench comprises introducing the process gas into a scrubbing column (10, 20, 30, 40, 50) into which in at least two different column portions respective aqueous, liquid scrubbing medium streams are introduced and run in countercurrent to the process gas.

2. Process according to claim 1 in which a scrubbing column (10, 20, 30, 40, 50) having a first column portion and a second column portion is used, wherein the second column portion is arranged above the first column portion, the process gas is introduced into a lower region of the first column portion and partly or completely allowed to ascend through the first column portion, from the first column portion into the second column portion and through the second column portion and in an upper region of the first column portion a first liquid scrubbing medium stream, and in an upper region of the second column portion a second liquid scrubbing medium stream, is introduced.

3. Process according to claim 2 in which the first scrubbing medium stream is introduced at a first temperature level into the first column portion and the second scrubbing medium stream is introduced at a second temperature level into the second column portion.

4. Process according to claim 3 in which the first temperature level is 50° C. to 90° C. and/or the second temperature level is 20° C. to 50° C.

5. Process according to claim 2 in which liquid is withdrawn from a lower region of the first column portion and partly or completely used for forming the first and/or the second scrubbing medium stream.

6. Process according to claim 2 in which the first column portion is separated from the second column portion by a liquid barrier tray 6.

7. Process according to claim 6 in which liquid is withdrawn from a lower region of the first column portion and partly or completely used in the formation of the first scrubbing medium stream and in which liquid is withdrawn from a lower region of the second column portion.

8. Process according to claim 7 in which the first and the second scrubbing medium stream contain predominantly water and in which the first scrubbing medium stream has a higher acetic acid content than the second scrubbing medium stream.

9. Process according to claim 2 in which a scrubbing column (30, 40, 50) having a third column portion above the second column portion is used, wherein the process gas is partly or completely allowed to ascend from the second column portion into the third column portion and through the third column portion, a third liquid scrubbing medium stream is introduced in an upper region of the third column portion.

10. Process according to claim 9 in which liquid is withdrawn from the lower region of the third column portion and partly or completely used in the formation of the second scrubbing medium stream.

11. Process according to claim 9 in which liquid is withdrawn from the lower region of the third column portion and partly or completely used in the formation of the third scrubbing medium stream.

12. Process according to claim 9 in which in the formation of the third scrubbing medium stream an externally supplied stream consisting predominantly of water and containing not more than 5000 ppmw of acetic acid is at least partly used.

13. Process according to claim 2 in which a scrubbing column (50) having a fourth column portion above the third column portion is used, wherein the process gas is partly or completely allowed to ascend from the third column portion into the fourth column portion and through the fourth column portion, a fourth liquid scrubbing medium stream is introduced in an upper region of the fourth column portion and liquid is withdrawn from a lower region of the fourth column portion.

14. Process according to claim 11 in which an aqueous lye or waste lye stream is used as the fourth scrubbing medium stream.

15. Plant (100) for producing ethylene adapted for forming an ethane- and oxygen-containing reaction input and for converting a portion of the ethane and of the oxygen in the reaction input into the ethylene and into acetic acid by oxidative dehydrogenation to obtain a process gas, wherein the process gas contains the unconverted portion of the ethane and of the oxygen, the ethylene and the acetic acid and also water and wherein means adapted for subjecting the process gas to a water quench are provided, characterized in that for water quenching a scrubbing column (10, 20, 30, 40, 50) having at least two different column portions is provided, means adapted for introducing the process gas into the scrubbing column (10, 20, 30, 40, 50) are provided and means adapted for introducing respective aqueous, liquid scrubbing medium streams into the at least two different column portions and running them in countercurrent to the process gas are provided.

16. Process according to claim 3 in which liquid is withdrawn from a lower region of the first column portion and partly or completely used for forming the first and/or the second scrubbing medium stream.

17. Process according to claim 4 in which liquid is withdrawn from a lower region of the first column portion and partly or completely used for forming the first and/or the second scrubbing medium stream.

18. Process according to claim 3 in which the first column portion is separated from the second column portion by a liquid barrier tray 6.

19. Process according to claim 4 in which the first column portion is separated from the second column portion by a liquid barrier tray 6.

20. Process according to claim 3 in which a scrubbing column (30, 40, 50) having a third column portion above the second column portion is used, wherein the process gas is partly or completely allowed to ascend from the second column portion into the third column portion and through the third column portion, a third liquid scrubbing medium stream is introduced in an upper region of the third column portion.

* * * * *